United States Patent
De Haan et al.

(10) Patent No.: US 9,480,434 B2
(45) Date of Patent: Nov. 1, 2016

(54) DISTORTION REDUCED SIGNAL DETECTION

(75) Inventors: Gerard De Haan, Helmond (NL); Ihor Olehovych Kirenko, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 256 days.

(21) Appl. No.: 14/239,371

(22) PCT Filed: Aug. 24, 2012

(86) PCT No.: PCT/IB2012/054304
§ 371 (c)(1),
(2), (4) Date: Feb. 18, 2014

(87) PCT Pub. No.: WO2013/030739
PCT Pub. Date: Mar. 7, 2013

(65) Prior Publication Data
US 2014/0206965 A1 Jul. 24, 2014

Related U.S. Application Data

(60) Provisional application No. 61/527,643, filed on Aug. 26, 2011.

(51) Int. Cl.
A61B 5/1455 (2006.01)
A61B 5/00 (2006.01)
(Continued)

(52) U.S. Cl.
CPC ........... *A61B 5/7246* (2013.01); *A61B 5/0082* (2013.01); *A61B 5/14551* (2013.01);
(Continued)

(58) Field of Classification Search
CPC .......................... A61B 5/1455; A61B 5/7271
See application file for complete search history.

(56) References Cited

U.S. PATENT DOCUMENTS 6,308,088 B1 * 10/2001 MacFarlane ......... A61B 5/0088
600/310
8,335,550 B2 * 12/2012 Segman ............. A61B 5/14552
600/310
(Continued)

FOREIGN PATENT DOCUMENTS

CN 101288103 A 10/2008
EP 2000082 A1 12/2008
(Continued)

OTHER PUBLICATIONS

Pratik Sahindrakar, "Improving Motion Robustness of Contact-less Monitoring of Heart Rate Using Video Analysis", Department of Mathmematics and Computer Science, Aug. 24, 2011, XP55051521, Eindhoven, NL, pp. 1-58.
(Continued)

*Primary Examiner* — Eric Winakur

(57) ABSTRACT

The present invention relates to a device and a method for extracting information from detected characteristic signals. A data stream (26; 124a, 124b, 124c) derivable from electromagnetic radiation (14) emitted or reflected by an object (12) is received. The data stream (26) comprises a continuous or discrete characteristic signal (76; 32a, 132b, 132c) including physiological information (100) and a disturbing signal portion 5 (94). The physiological information (100) is representative of at least one at least partially periodic vital signal (20; 156). The disturbing signal portion (94) is representative of at least one of an object motion portion and/or a non-indicative reflection portion. The characteristic signal (76; 132a, 132b, 132c) is transferred by converting at least three absolute components (92a, 92b, 92c) of the characteristic signal (76; 132a, 132b, 132c) related to respective 10 additive channels (74a, 74b, 74c) to at least two difference components (102; 142a, 142b) of the characteristic signal (76; 132a, 132b, 132c), wherein each of the at least two difference components (102; 142a, 142b) can be derived through a respective arithmetic transformation considering at least two of the at least three absolute components (92a, 92b, 92c), wherein the arithmetic transformation comprises additive and subtractive coefficients. Consequently, the 1 disturbing signal portion (94) can beat least partially suppressed in the transferred signal (32; 50).

20 Claims, 8 Drawing Sheets

(51) Int. Cl.
  *G06K 9/00* (2006.01)
  *G06T 7/00* (2006.01)
  *A61B 5/024* (2006.01)

(52) U.S. Cl.
  CPC ........... *A61B5/7207* (2013.01); *G06K 9/0051* (2013.01); *G06K 9/00503* (2013.01); *G06T 7/0016* (2013.01); *A61B 5/0077* (2013.01); *A61B 5/02416* (2013.01); *A61B 5/7232* (2013.01); *G06K 2209/05* (2013.01); *G06T 2207/30076* (2013.01)

(56) References Cited

U.S. PATENT DOCUMENTS

| | | |
|---|---|---|
| 2003/0088164 A1 | 5/2003 | Stetson |
| 2006/0058683 A1 | 3/2006 | Chance |
| 2006/0293574 A1 | 12/2006 | Norris |
| 2007/0219439 A1 | 9/2007 | Vilser et al. |

FOREIGN PATENT DOCUMENTS

| | | |
|---|---|---|
| WO | 2007022413 A2 | 2/2007 |
| WO | 2011021128 A2 | 2/2011 |
| WO | 2011042858 A1 | 4/2011 |

OTHER PUBLICATIONS

Ming-Zher Poh et al, "Non-contact, automated cardiac pulse measurements using video imaging and blind source separation", Optiocs Express, vol. 18, No. 10, May 7, 2010, pp. 10762-10774, XP002685985, DOI: 10.1364/OE.18.010762.

Markus Hulsbusch et al, "eIN Bildgestutztes, Funktionelles Verfahren Zur Optoelektronischen Erfassung Der Hautperfusion", Dissertation Technischen Hochschule Aachen, Jan. 28, 2008, pp. 1-145, XP007913039, Section 6.2.1.

Wim Verkruysse et al, "Remote plethysmorgraphic imaging using ambient light", Optics Express, Optical Society of America, Washington, D.C., USA, vol. 16, No. 26, pp. 21434-21445.

\* cited by examiner

DISTORTION REDUCED SIGNAL DETECTION

CROSS-REFERENCE TO PRIOR APPLICATIONS

This application is the U.S. National Phase application under 35 U.S.C. §371 of International Application No. PCT/IB2012/054304, filed on Aug. 24, 2012, which claims the benefit of U.S. Provisional Patent Application No. 61/527,643, filed on Aug. 26, 2011. These applications are hereby incorporated by reference herein.

FIELD OF THE INVENTION

The present invention relates to a device and method for extracting information from characteristic signals, wherein the characteristic signals are embedded in a data stream derivable from electromagnetic radiation, in particular wherein the data stream comprises a continuous or discrete characteristic signal including physiological information and a disturbing signal portion, the physiological information being representative of at least one at least partially periodic vital signal of an object of interest, the disturbing signal portion being representative of at least one of an object motion portion and/or a non-indicative reflection portion. The invention further addresses distortion reduced signal detection.

BACKGROUND OF THE INVENTION

WO 2011/021128 A2 discloses a method and a system for image analysis, including:
obtaining a sequence of images;
performing a vision-based analysis on at least one of the sequence of images to obtain data for classifying a state of a subject represented in the images;
determining at least one value of a physiological parameter of a living being represented in at least some of the sequence of images, wherein the at least one value of the physiological parameter is determined through analysis of image data from the same sequence of images from which the at least one image on which the vision-based analysis is performed is taken; and
classifying a state of the subject using the data obtained with the vision-based analysis and the at least one value of the physiological parameter.

The document further discloses several refinements of the method and system. For instance, the use of remote photoplethysmographic (PPG) analysis is envisaged. In general, in the field of image processing enormous progress was made in that profound analyses of the recorded data were enabled. In this context, it could be envisaged to extract information from recorded data in a way so as to enable detailed conclusions regarding the physical condition or even the well-being of an observed living individual.

WO 2011/042858 A1 discloses a further method and system addressing processing a signal including at least a component representative of a periodic phenomenon in a living being. Additional basic approaches to remote photoplethysmography are described in Verkruysse, W. et al (2008), "Remote plethysmographic imaging using ambient light" in Optics Express, Optical Society of America, Washington, D.C., USA, vol. 16, no. 26, pp. 21434-21445.

However, the recorded data, such as captured reflected or emitted electromagnetic radiation, especially recorded image frames, always comprises, beside of the desired signal to be extracted therefrom, further signal components deriving from overall disturbances, by way of example, such as noise due to changing luminance conditions or a movement of observed objects. Hence, a detailed precise extraction of the desired signals still poses major challenges for the processing of such data.

Although considerable progress in the field of computing performance has been made, it is still a challenge to provide for instant image recognition and image processing enabling immediate, so to say, on-line detection of desired vital signals. This applies in particular to mobile device applications commonly lacking of sufficient computing power. Furthermore, data transmission capacity can be restricted in several applications.

A possible approach to this challenge may be directed to providing well-prepared and steady ambient conditions when capturing a signal of interest in which the desired signal component is embedded so as to minimize disturbing signal components overlaying the signal. However, such laboratory conditions cannot be transferred to everyday field applications as high efforts and preparation work would be required therefor.

After all, vital signal detection is made even more difficult when amplitudes and/or nominal values of disturbing signal components are much larger than amplitudes and/or nominal values of desired signal components to be extracted. Potentially, the magnitude of difference between the respective components can be expected to even comprise several orders.

SUMMARY OF THE INVENTION

It is therefore an object of the present invention to provide a system and a method for extracting information from detected characteristic signals providing further refinements facilitating obtaining the desired signals with higher accuracy.

Furthermore, it would be advantageous to provide a device and method even adapted for enabling an extraction of the desired signals under considerably poor ambient conditions, e.g. small signal-to-noise ratio, varying luminance conditions and/or steady or even unsteady movements of the object to be observed. It would be further advantageous to provide a device adapted for being less susceptible to disturbances influencing the captured signals to be processed and analyzed.

In a first aspect of the present invention a system for extracting information from detected characteristic signals is presented, the system comprising:
an interface for receiving a data stream derivable from electromagnetic radiation reflected by an object, the data stream comprising a continuous or discrete characteristic signal including physiological information and a disturbing signal portion, the physiological information being representative of at least one at least partially periodic vital signal, the disturbing signal portion being representative of at least one of an object motion portion and/or a non-indicative reflection portion, the characteristic signal being associated with an additive signal space, the signal space comprising additive channels for representing the characteristic signal,
a converter means for transferring the characteristic signal by converting at least three absolute components of the characteristic signal related to respective additive channels to at least two difference components of the characteristic signal, wherein each of the at least two difference components can be derived through a respective arithmetic transformation considering at least two of the at least three absolute components, wherein the arithmetic transformation comprises additive and subtractive coefficients, the disturbing signal portion being at least partially suppressed in the transferred signal, an extractor means for extracting the vital signal from the transferred signal, preferably the vital signal is extracted under consideration of an additive or subtractive expression or a ratio of the at least two difference components.

Object motion and changing illumination conditions pose major challenges for signal detection, in particular when instant signal detection is demanded. For instance, detected illumination changes can be caused by object motion. This applies in particular when object tracking is subjected to restrictions, such as time delay, or even when illumination is only consistent in a very small area. Furthermore, illumination conditions can deteriorate due to unsteady illumination sources, e.g., varying ambient light.

A considerable portion of illumination-related disturbances can be explained by specular reflection. Specular reflectance is the "perfect" reflection of incident radiation at an interface. Basically, an incident ray corresponds to a reflected ray. An angle of reflection equals an angle of incidence. In other words, specular reflection implies mirror-like reflection at surfaces and interfaces. Furthermore, the reflected ray is highly indicative of the source of electromagnetic radiation, namely the illumination source. This relationship has been utilized.

It is understood that mainly diffuse reflection provides the desired vital signals. Diffuse reflection substantially comprises body reflection rather than interface reflection. For instance, body reflection is influenced by slight changes of the color of an area of interest of the body. Color changes can be caused, inter alia, by vascular pulsation due to blood circulation. The desired vital signals can be derived therefrom. Furthermore, incident radiation can be absorbed to some extent. However, the detectable reflected signals most probably comprise a disturbing specular reflection portion. Specular reflection basically "mirrors" incident radiation without being influenced by object properties present under the interface, e.g., the top surface of the skin. Especially perspiring skin areas and oily or greasy skin areas are highly susceptible to specular reflections. Under certain circumstances, e.g., sports practice, workouts, physically demanding work, or even due to illness, a huge portion of electromagnetic radiation reflected by the object can be related to specular reflectance. Thus, the characteristic signal is supposed to have a poor, i.e. reasonably small, signal-to-noise ratio.

Further adverse effects on the signal-to-noise ratio can occur when an object of interest has a dark skin tone. Basically, dark colors absorb a larger part of incident radiation than bright colors. Therefore, objects having a light skin tone absorb less radiation. As only reflected radiation can carry the desired signals, the signal-to-noise ratio is even further worsened for dark skin.

By way of example, the data stream can be captured by means of a charge-coupled device (CCD) sensor. Usually, a point of interest, e.g. captured by a single CCD pixel, or a pixel array, covers radiation portions attributable to non-indicative specular reflection and indicative diffuse reflection. Furthermore, when summarizing captured radiation of a pattern of pixels, most likely a combination of (diffuse) scattering reflection plus perfect (specular) reflection can be contained in the input data.

The present invention is based on the insight that, when applying an additive signal space, the characteristic signal is basically composed of components related to distinct channels, or, so to say, axes. The additive signal space can be linked to a derivative signal space or signal model. Basically the derivative signal space utilizes a different approach for composing the characteristic signal. Amongst other possible components, the derivative signal model, or, signal representation, relies on difference components rather than absolute components. Advantageously, the difference components enable a signal representation wherein specular reflection can be suppressed, at least to a certain extent.

In other words, when transferring the characteristic signal to the derivative signal model, en passant, considerable parts of the disturbing signal portion can be eliminated from the characteristic signal. The characteristic signal can be at least partially compensated for object motion and/or a non-indicative body reflection. The signal-to-noise ratio can be improved in this way. Thus, downstream signal analysis can be simplified, even under considerably challenging conditions. Furthermore, a required data volume can be reduced as fewer "channels" are required for carrying the desired vital signals.

It goes without saying that further signal optimization measures can be applied to the data stream comprising the characteristic signals. These measures can comprise motion compensation, pattern detection, e.g., face detection, or normalization measures. Normalization can render signal components at least partially independent from overall disturbances. In the context, it is reminded that under everyday condition the signals of interest are considerably small compared to the non-indicative disturbances.

The data stream can comprise a data sequence, e.g., a series of image frames comprising color information, such as RGB images. The image frames can represent the object of interest and further elements. Basically, the further elements are not indicative of the desired signals to be extracted from the data stream.

There exist several embodiments of the converter means and the extractor means. In a first, fairly simple embodiment both, the detector means and the converter means, are embodied by a processing unit, in particular a processing unit of a personal computer or a mobile device, which is driven by respective logic commands. Such a processing unit may also comprise suitable input and output interfaces.

However, in the alternative, each of the converter means and the extractor means can be embodied by a separate processing unit driven or driveable by respective commands. Hence, each respective processing unit can be adapted to its special purpose. Consequently, a distribution of tasks may be applied, wherein distinct tasks are processed, for instance, executed on a single processor of a multi-processor processing unit, or, again referring to a personal computer, image processing-related tasks are executed on an image processor while other operational tasks are executed on a central processing unit.

It goes without saying that the subtractive expression also can be considered as an additive expression comprising negative coefficients, at least partially.

According to a further aspect of the invention, the converter means is further adapted for transferring the characteristic signal under consideration of the arithmetic transformation, wherein the arithmetic transformation comprises an at least partially subtraction of at least one of the at least three absolute components from the remaining absolute components, and wherein the arithmetic transformation for each of the at least two difference components comprises coefficients at least substantially summing to zero.

For instance, the transformation can correspond to the following scheme $$\begin{pmatrix} \Delta_1 \\ \Delta_2 \end{pmatrix} = \begin{bmatrix} a_1 & a_2 & a_3 \\ b_1 & b_2 & b_3 \end{bmatrix} \cdot \begin{pmatrix} R \\ G \\ B \end{pmatrix},$$

wherein $(\Delta_1 \ \Delta_2)^T$ represents the difference components, wherein $(R \ G \ B)^T$ represents the absolute components, wherein $a_1$, $a_2$, $a_3$ and $b_1$, $b_2$, $b_3$ represent the coefficients, and wherein $a_1+a_2+a_3=0$ and $b_1+b_2+b_3=0$. The vector $(R \ G \ B)^T$ can be represented in an additive signal space.

By way of example, in a preferred embodiment the coefficients may have the following values: $a_1=1$, $a_2=-1$, $a_3=0$ and $b_1=1$, $b_2=1$, $b_3=-2$.

In another preferred embodiment the coefficients may take the following values: $a_1=0.5$, $a_2=-0.5$, $a_3=0$ and $b_1=0.25$, $b_2=0.25$, $b_3=-0.5$.

These embodiments enable a considerably improved signal-to-noise ratio facilitating further signal analyses. In this connection, an optional generalized supplemental expression for the terms $\Delta_1$ and $\Delta_2$ could read as follows: $\Delta_1^*=\cos(\phi)\Delta_1+\sin(\phi)\Delta_2$ and $\Delta_2^*=\sin(\phi)\Delta_1+\cos(\phi)\Delta_2$, wherein $0\le\phi\le2\pi$. Hence, adequate difference components can be chosen from a possible set of derived difference component terms $\Delta_1^*$ and $\Delta_2^*$ still meeting the requirements outlined above. Furthermore, for some embodiments it can be preferred that both difference component terms $\Delta_1$ and $\Delta_2$ (or, $\Delta_1^*$ and $\Delta_2^*$) determined through the arithmetic transformation eventually have like signs.

The foregoing scheme can be further expanded to $$\begin{pmatrix} L \\ \Delta_1 \\ \Delta_2 \end{pmatrix} = \begin{bmatrix} l_1 & l_2 & l_3 \\ a_1 & a_2 & a_3 \\ b_1 & b_2 & b_3 \end{bmatrix} \cdot \begin{pmatrix} R \\ G \\ B \end{pmatrix}$$

in case it is preferred to maintain luminance information. The coefficients $l_1$, $l_2$, $l_3$ can fulfill the requirement $l_1+l_2+l_3=1$. For instance, the coefficients can have the following values: $l_1=0.33$, $l_2=0.33$, $l_3=0.33$. However, luminance information is no longer necessarily required for extracting the desired vital signals.

Needless to say, for some applications the symbol "=" can be readily replaced by "≈" without departing from the scope of the present disclosure.

For instance, established PPG approaches basically can make use of a ratio of two distinct (absolute) signal components, e.g. the ratio between red and infrared signals, or the ratio between red and green signals. For further consideration, the ratio can be plotted over time. Slight periodic changes of the ratio can allow an estimation of the desired signals.

Assuming that the applied absolute signals are simultaneously influenced (e.g., identically influenced by white illuminant) by varying illumination conditions (e.g., varying specular reflection), it is suggested to base the signal detection on a ratio of difference signals to be derived from the absolute signals. This aspect comes from the insight that non-indicative specular reflection is basically similarly present in the absolute signals, e.g. a red signal, a green signal and a blue signal. When at least two of these signals are compared, e.g., when a difference signal is derived therefrom, it can be assumed that specular reflection is at least substantially suppressed in the difference signal.

In other words, in terms of vector representation, the absolute signals, namely the at least three absolute components, can be considered components of the vector representing the characteristic signal. Each of the at least two difference components can be obtained by applying the named transformation to at least two of the at least three absolute components. Needless to say, each of the at least three absolute components should be taken into account for the determination of at least one of the at least two difference components. Hence, when looked at together, the difference components can still represent each of the original absolute components, at least to a certain extent. The characteristic signal vector having at least three components can be replaced for further signal detection measures by a difference vector comprising a smaller number of components, e.g., decreased by one when compared with the components of the characteristic signal vector. The "axed" component represents the specular reflectance portion, at least to a certain extent.

Besides that, however, the characteristic signal vector also can be considered a linear combination of an indicative vector representing the physiological information of interest and a non-indicative vector representing the specular reflection portion.

It goes without saying that further disturbing portions can be contained in the characteristic signal vector. However, the present invention primarily addresses specular reflection issues and object motion issues related thereto.

According to a further embodiment of the device, the signal space is an additive color signal space, wherein the at least three absolute components represent three distinct color components indicated by the additive channels, wherein the additive channels are related to defined spectral portions.

For instance, an RGB signal space may be applied. Alternative signal spaces may comprise or be derived from CIE XYZ, HSV, HSL, sRGB and xvYCC signals. Also derivates thereof can be utilized. It should be noted that basically linear RGB signals can be utilized for the desired signal detection. Therefore, non-linear signal spaces (e.g. gamma corrected signals) can be transformed accordingly. It can be further envisaged to combine several distinct signal spaces at least partially so as to provide a broader spectral basis for the required analyzing processes. For instance, so-called RGBY signals can be applied as well. In an RGBY signal space in addition to red, green and blue also yellow signals can carry color information.

In case the input data stream is related to a subtractive color model, e.g., CMYK, the data can be transferred accordingly so as to arrive at an additive signal space.

Further spectral components can be utilized for extracting the desired vital signal(s) from the data stream. In this connection, also infrared radiation components can be applied. For instance a ratio between red and infrared signals can be highly indicative of the desired signals. Also infrared radiation can undergo specular reflectance.

Furthermore, the signal space can be indicative of luminance information and chrominance information, the chrominance information being representable by the at least two difference components.

For detecting the desired signal(s) of interest, it is preferred that mainly the chrominance information is utilized. In this way, specular reflections substantially influencing luminance information can be "ignored". In other words, the use of chrominance information represented by the (color)

difference signals can render the transferred signal substantially independent of the mainly disturbing luminance component. It should be understood that preferably linear signals are utilized. Non-linear signals, e.g., gamma corrected signals, can be (re)transformed accordingly.

According to an even further embodiment, the luminance information is substantially aligned with a luminance index element in the signal space, the luminance index element being substantially indicative of a selected source of electromagnetic radiation.

Preferably the luminance index element represents an expected or measured light source characteristic, e.g., a light source color or a color temperature of a radiation source.

The source of electromagnetic radiation can be embodied by artificial light sources, sun light, radiation sources emitting radiation having non-visible components, or combinations thereof. The radiation can be guided directly to the object of interest. Also indirect radiation, e.g. ambient light, is applicable.

For most applications it can be fairly assumed that the radiation source, namely the light source, emits basically plain white light. Hence, assuming an additive signal space composed of three color channels, the luminance index element can be represented by a diagonal vector traversing the signal space. For instance, a black point indicating the smallest luminance value can be embodied by a zero point of the signal space (0, 0, 0). The black point can coincide with the common initial point of the axes representing the additive components, e.g., red, green, and blue. Diagonally opposite of the black point a white point can be disposed in the signal space. The white point can denote the point of the largest luminance value. In case the signal space is a "unitary" signal space, the white point can be embodied by the point (1, 1, 1). The white point can further denote the end point of the luminance index element. So, given these assumptions, the luminance index element can be embodied by the vector $(1\ 1\ 1)^T$ in the signal space.

According to a further aspect of the device, the at least two difference components are substantially orthogonal to the luminance index element, preferably the at least two difference components are substantially orthogonal to each other.

This applies in particular when the respective components are handled in terms of vector representation. A diagonal plane traversing the signal space and being substantially orthogonal to the luminance index element can be considered a chrominance plane. The chrominance plane represents a "slice" of the signal space being substantially independent of luminance information.

According to a further embodiment of the device, the at least one at least partially periodic vital signal is selected from the group consisting of heart rate, heart beat, respiration rate, heart rate variability, Traube-Hering-Mayer waves, and oxygen saturation.

Advantageously, at least some of these vital signals can be converted into one another. Slight oscillations of the characteristic signals can be analyzed and interpreted so as to arrive at the detection of the desired vital signals. Furthermore, it is understood that, in general, the desired vital signal(s) can be derived directly or indirectly from at least one at least partially periodic signal the object of interest exhibits. It goes without saying that the device and method of the invention can be combined with further detecting and analyzing measures so as to further enhance the signal extraction.

As mentioned above, photoplethysmography can make use of a ratio of two distinct (absolute) signal components, e.g. the ratio between red and green signals. For instance, a normalization can be applied wherein the red and green signals are divided by their respective (temporal) mean values. This approach applies in particular when the absolute components are unlikely to become zero. Under usual conditions neither a red (or mean red) signal nor a green (or, mean green) signal will become zero so that division by zero is unlikely to happen. Basically, such an approach can be applied to difference components as well.

However, under certain circumstances a ratio of difference components (as well as a ratio of absolute components) can lead to an erroneous division-by-zero term. This applies in particular when selected (temporal frequency) portions of the difference components, as well as of their temporal mean values, are either enhanced or suppressed. For instance, a removal of non-indicative spectral portions may lead to processed difference components no longer exhibiting "steady" portions. Therefore, a mean value thereof potentially can become zero. Thus, common normalization under consideration of mean values can face a division-by-zero issue. Therefore, a simple consideration of the ratio between two difference components can face further challenges. A possible approach to this issue can be a transformation of the ratio (quotient) term. For instance, logarithmic identities can be considered allowing an alternative representation of the logarithm of the quotient, namely a difference between the logarithm of the numerator of the quotient and the logarithm of the denominator of the quotient. Further considering the Taylor extension of the logarithms and assuming expected values of the logarithmic terms, an (inverse) additive combination of the two difference components still enables a detection of the desired signals. In this context, it is referred to respective equations stated below in connection with detailed description of an exemplary embodiment. It is further reminded that the desired signals, e.g., the heart rate, basically can be extracted by analyzing slight temporal variations of the characteristic signals rather than absolute values thereof.

However, according to an alternative approach, the desired vital signals indeed can be extracted under consideration of a ratio between the at least two difference components. In this connection, when normalizing, facing the division-by-zero issue mentioned above, it is suggested to apply a normalization of the difference components relying on a division by their respective standard deviation rather than their respective mean value. This approach is based on the insight that amplitudes of the utilized difference components are at least partially proportional to their mean values.

Furthermore, in yet another embodiment, e.g., when a subtractive expression of the difference components is utilized, it is further preferred that the device comprises a weighting means for weighting the at least two difference components so as to derive a weighted transferred signal from the transferred signal under consideration of at least two weighted difference components, preferably the weighting is directed to minimize a spread of the weighted transferred signal.

The weighting means can contribute to further improvement of the signal detection. The weighting means can be comprised between the converter means and the extractor means. Also the weighting means can be embodied by the common processing unit.

The spread can be also referred to as statistical dispersion, statistical variability or variation. For instance, the spread can be represented by variance or standard deviation values.

As for the difference component approach of the invention, it is further preferred that the signal of interest is derived under consideration of a weighted sum (or difference) of the at least two difference signals. The weighting means can allow for instant determination of a weighting factor. Further approaches can be envisaged without departing from the scope of the present disclosure.

This embodiment is further developed in that the weighting comprises a determination of a deviation value, preferably a standard deviation, of each of the at least two difference components, wherein the deviation value of each of the at least two difference components is determined under consideration of temporal variations thereof over a moving window applied to a sequence of each of the at least two difference components.

The deviation value can be indicative of statistical dispersion of each of the at least two difference components. In this way, the resulting weighted sum can have a considerably small variance. Hence, signal detection can be further improved. This applies in particular when overall disturbances (i.e. not attributable to specular reflection) are considerably large compared to the desired signals of interest.

According to an even further embodiment of the device, at least one of the converter means and extractor means is further adapted to normalize the transferred signal under consideration of a deviation value thereof, preferably a standard deviation, over a moving window applied to a sequence of the transferred signal.

Hence, the desired signals can be further enhanced by removing a statistical dispersion indicative of disturbing overall deviation. In particular, the amplitude of the signal of interest can be further "stabilized" in this way.

According to another aspect, the device further comprises an analyzing means, the analyzing means being comprised in the extractor means or coupled thereto, wherein the analyzing means is adapted for a frequency analysis of the at least one at least partially periodic vital signal, preferably the analyzing means is further adapted for filtering the processed transferred signal and for enhancing a signal component at a bandwidth between 0.2 Hz and 10 Hz, preferably between 0.5 Hz and 3.5 Hz. In this way, even further disturbing signal components non-indicative of the desired vital signals can be removed from the data stream.

According to an even further aspect, the device comprises a processing unit comprising the converter means, the extractor means and the analyzing means. Also the weighting means can be embodied by the processing unit. The processing unit can be part of a personal computer, a mobile device, or even a mobile phone.

According to another embodiment of the device, it is preferred that at least one of the converter means, the extractor means and the analyzing means is further adapted for delivering a compressed output signal, wherein the output signal comprises the luminance information represented by a luminance signal and the chrominance information represented by the at least two difference components, wherein selective compression rates are applied to the luminance information and the chrominance information, wherein the chrominance information is compressed at a lower compression factor than the luminance information.

Compression at a lower compression factor is equivalent to compression at a higher data rate (bit rate).

Compression for each of the output components can be carried out utilizing constant bit rates or variable bit rates. Distinct compression rates take account of required information density facilitating signal detecting. As luminance information basically can be neglected for detecting and computing of the desired signals, it is not necessary to keep and store slightest signal changes of the luminance information. On the other hand, the signals of interest are mainly represented by small changes of the difference components. Hence, it is advisable to apply a higher bit rate for the chrominance information. Eventually, the processed data can be stored or buffered. Additional post processing can be enabled. Furthermore, in case also the luminance information is maintained, subsequent representation of the (processed) data stream, e.g., video representation, is still enabled. Therefore, it can be sufficient to maintain a single format of the received and processed data.

It is further preferred, that the device comprises motion compensation means. Motion compensation can be directed to at least one of object motion and sensor means motion, namely camera motion.

In a further aspect of the present invention a method for extracting information from detected characteristic signals is presented, comprising the steps:

receiving a data stream derivable from electromagnetic radiation reflected by an object, the data stream comprising a continuous or discrete characteristic signal including physiological information and a disturbing signal portion, the physiological information being representative of at least one at least partially periodic vital signal, the disturbing signal portion being representative of at least one of an object motion portion and/or a non-indicative reflection portion, the characteristic signal being associated with an additive signal space, the signal space comprising additive channels for representing the characteristic signal, transferring the characteristic signal by converting at least three absolute components of the characteristic signal related to respective additive channels to at least two difference components of the characteristic signal, wherein each of the at least two difference components can be derived through a respective arithmetic transformation considering at least two of the at least three absolute components, wherein the arithmetic transformation comprises additive and subtractive coefficients, the non disturbing signal portion being at least partially suppressed in the transferred signal, extracting the vital signal from the transferred signal, preferably the vital signal is extracted under consideration of an additive or subtractive expression or a ratio of the at least two difference components.

Advantageously, the method can be carried out utilizing the device for extracting information of the invention.

According to an even further aspect of the invention a computer program is presented, the computer program comprising program code means for causing a computer to carry out the steps of the method for extracting information of the invention when said computer program is carried out on a computer.

Preferred embodiments of the invention are defined in the dependent claims. It shall be understood that the claimed method has similar and/or identical preferred embodiments as the claimed device and as defined in the dependent claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
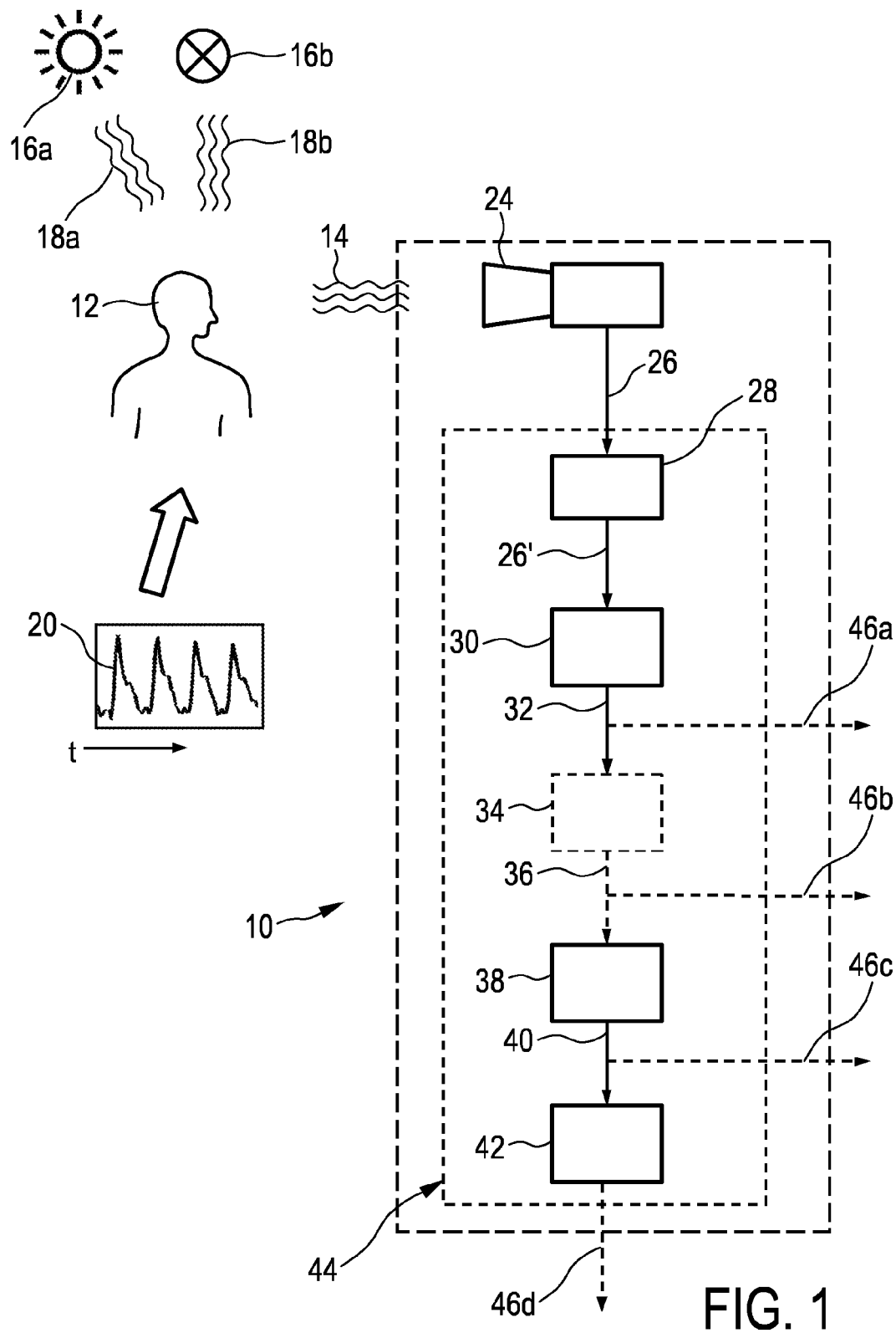
FIG. 1 shows a schematic illustration of a general layout of a device in which the present invention can be used.

FIG. 1 shows a schematic illustration of device for extracting information which is denoted by a reference numeral 10. For instance, the device 10 can be utilized for recording image frames representing an object 12. The image frames can be derived from electromagnetic radiation 14 reflected by the object 12. The object 12 can be a human being or animal, or, in general, a living being. Furthermore, the object 12 can be part of a human being highly indicative of a desired signal, e.g., a face portion, or, in general, a skin portion.

A source of radiation, such as sunlight 16a or an artificial radiation source 16b, also a combination of several radiation sources can affect the object 12. The radiation source 16a, 16b basically emits incident radiation 18a, 18b striking the object 12. For extracting information from the recorded data, e.g. a sequence of image frames, a defined part or portion of the object 12 can be detected by a sensor means 24. The sensor means 24 can be embodied, by way of example, by a camera adapted to capture information belonging to at least a spectral component of the electromagnetic radiation 14. It goes without saying that the device 10 also can be adapted to process input signals, namely an input data stream, already recorded in advance and, in the meantime, stored or buffered. As indicated above, the electromagnetic radiation 14 can contain a continuous or discrete characteristic signal which can be highly indicative of at least one at least partially periodic vital signal 20. The characteristic signal can be embodied by an (input) data stream 26. In FIG. 1 the vital signal 20 may allow several conclusions concerning heart rate, heart beat, heart rate variability, respiratory rate, or even oxygen saturation.

Known methods for obtaining such vital signals may comprise tactile heart rate monitoring, electrocardiography or pulse oximetry, for instance. To this end, however, obtrusive monitoring was required. As indicated above, an alternate approach is directed to unobtrusive remote measuring utilizing image processing methods.

The data stream 26 comprising the continuous or discrete characteristic signal can be delivered from the sensor means 24 to an interface 28. Needless to say, also a buffer means could be interposed between the sensor means 24 and the interface 28. Downstream of the interface 28 a converter means 30 is provided which is adapted to transfer the characteristic signal still embedded in the received data stream 26'. The transformation can comprise an arithmetic transformation resulting in difference signals rather than absolute signals. Difference signals are less indicative of disturbing components of the characteristic signals in the data stream 26. Hence, a transferred signal 32 can be output for subsequent analyses.

Further, a weighting means 34 can follow which is adapted for weighting an expression comprising the difference components. The weighting means 34 is illustrated by a dashed line indicating that the weighting means 34 can be considered optional. An optionally weighted transferred signal is denoted by a reference numeral 36.

Downstream, an extractor means 38 can be comprised in the device 10. The extractor means 38 can be adapted for extracting the vital signal 20 from at least one of the transferred data stream signal 32 and the weighted transferred data stream signal 36. For instance, an extracted signal can be indicative of an additive or a subtractive expression of two of the difference components. Thus, a ratio of the difference components can be expressed in a simplified way.

Furthermore, an analyzing means 42 can follow to which the extracted signal 40 can be delivered from the extractor means 38. The analyzing means 42 can be adapted for further processing of the extracted signal 40, e.g., detection of a dominant signal peak, such as a heart rate indicative frequency peak. In this connection, the analyzing means 42 can be applied for isolating and enhancing the desired signal component even more indicative of the vital signal 20 of interest from the overall signal delivered thereto.

The converter means 30, the weighting means 34, the extractor means 38, and the analyzing means 42 can be jointly embodied by a common processing unit 44, e.g. a central processing unit having a single processor or multiple processors. Also the interface 28 can be connected thereto in a common processing unit 44 housing the respective subcomponents. By way of example, the processing unit 44 can be embodied by a personal computer driven by respective logic commands. In case the sensor means 24 is also jointly connected to the interface 24 by means of hardware, a capturing unit arranged at a higher level may house the respective subcomponents.

However, in the alternative, it can be envisaged to combine a separate sensor means 24 with the processing unit 44. This connection can be established by means of cable links or by means of wireless links. In place of the sensor means 24 also a storage means comprising prerecorded data could be connected to the processing unit 44.

As indicated above, the converter means 30 can be further adapted to carry out some preprocessing of the received data so as to already enhance the signal-to-noise ratio in preparation for subsequent analyses addressed to the desired vital signals.

Dashed arrows 46a, 46b, 46c, 46c illustrate that processed data can be output at several stages of the device 10 for further processing outside of the device 10. The data that can be delivered via the arrows 46a, 46b, 46c, 46c can be stored or buffered for subsequent processing. Furthermore, output data can be utilized for representing the (image) data stream.

The following section describes an exemplary approach to remote photoplethysmography utilizing several aspects of the device and method of the invention. It should be understood that single steps and features of the shown approach can be extracted from the context of the approach. These steps and features can be therefore part of separate embodiments still covered by the scope of the invention.

As outline above, unobtrusive vital signal monitoring using a video camera, also referred to as remote photoplethysmography, has been demonstrated. Basically, algorithms can register the average skin-tone of an object, e.g., a person, which varies with the blood volume and blood oxygenation.

In a classical (also non-remote) photoplethysmography approach, the heartbeat can be detected in a normalized ratio of red and green color components. Also a ratio of red and infrared spectral components can be utilized. Basic photoplethysmography devices may comprise obtrusive attachments to be applied to a fingertip or an earlobe of an object to be observed. Hence, these approaches may imply an uncomfortable feeling when applied.

The named normalization can be directed to time based normalization. For instance, the red color components can be normalized by calculating:

$$R_n(i) = \frac{R(i)}{\sum_{i=k}^{n} R(i)} = \frac{R(i)}{\overline{R(i)}}, \quad (1)$$

$$k \leq i \leq n$$

and similarly for green, where n–k can be chosen such that at least a number of heartbeats is covered.

The normalization can be directed to make the heartbeat amplitude independent of the strength and color of the illuminant. The heartbeat signal itself results in:

$$HB(i) = \frac{R_n(i)}{G_n(i)} = \frac{R(i)}{G(i)} \cdot \frac{\overline{G(i)}}{\overline{R(i)}} - 1 \quad (2)$$

In this way, illumination independent results can be achieved provided the observed red and green signals are the result of light passing through the skin. These spectral components are highly indicative of the desired signals. In a non-remote photoplethysmographic approach monitoring conditions are steady. Ambient light and distortions due to further illumination variations basically can be neglected. Usually, non-remote photoplethysmographic devices comprise standard lights emitting radiation guided directly to a portion of interest of the object to be monitored. As the devices can be closely attached to respective skin areas, disturbing luminance variation caused by remote lights can be avoided.

Under these "laboratory" conditions the ratio of red and green is mainly determined by the color of the skin, which slightly fluctuates with the heartbeat, but can be considered constant for the mean ratio of red and green, as long as the spectrum of the (device inherent) illuminant is stable.

Figure 2:
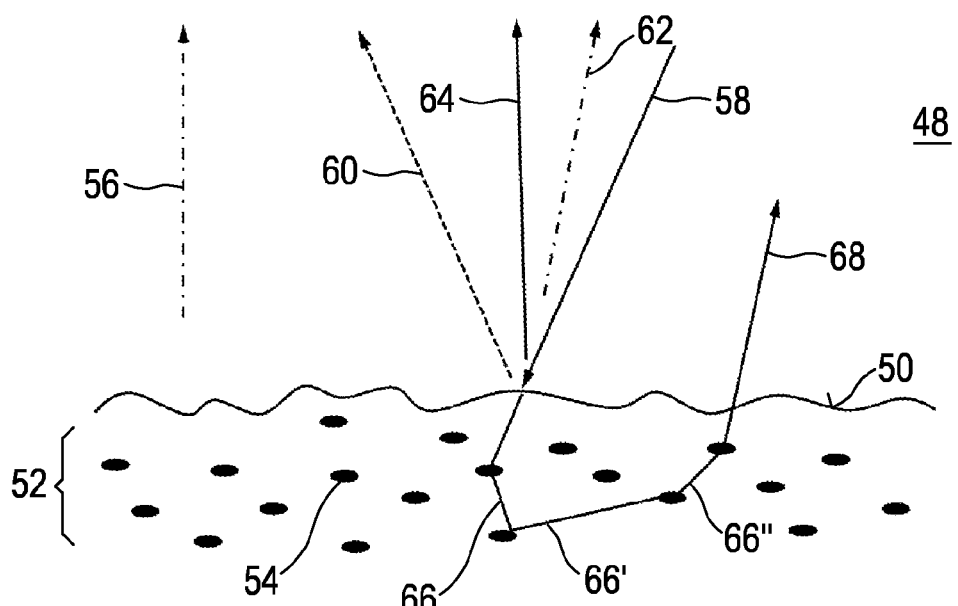
FIG. 2 shows a schematic illustration of a reflectance model utilizing a body reflection and interface reflection approach.

However, in practice, when applying remote photoplethysmographic approaches, e.g. a camera based PPG system, the light reflected from the skin basically comprises two components that can be described by the so-called dichromatic reflection model. In this connection, reference is made to FIG. 2 illustrating reflection of incident radiation 58 at an interface 50 between two media 48, 52. Reference numeral 48 denotes air through which incident radiation 58 is transmitted. Reference numeral 52 denotes a skin tissue to which incident radiation 58 is directed. An interface 50 is interposed between the air 48 and the skin tissue 52. The interface 50 can be considered as the top surface of the skin. The skin tissue 52 may comprise colorant 54 which slightly fluctuates with the signal of interest, e.g., the heart rate. The interface or top surface 52 may comprise a macroscopic surface normal 56 and microscopic surface normals 62, the latter attributable to microscopic surface unevenness. Hence, even incident radiation 58 subjected to (perfect) specular reflection at the interface 50 can be reflected at an reflection angle corresponding to the microscopic surface normal 62 rather than the macroscopic surface normal 56. The reflected radiation is denoted by reference numeral 64. A reflected radiation to be expected with knowledge of the macroscopic surface normal 56 is denoted by reference numeral 60. However, for the following elucidation the microscopic surface normal 62 can be equated with the macroscopic surface normal 56.

Furthermore, a considerable component of the incident radiation 58 is reflected by skin tissue colorant 54 rather than the interface 50. The reflection may comprise multiple reflections as indicated by reference numerals 66, 66', 66". As skin tissue colorant 54 is distributed inhomogeneously in the skin tissue and respective colors may vary over time, the so-called body reflection can be considered substantially diffuse reflection. Reflected radiation due to body reflection is denoted by reference numeral 68. Thus, beside of the specular reflection component 64 also a diffuse scattered reflection component 68 can be reflected by the object of interest.

Hence, a part of incident light or radiance is reflected by a diffuse reflection component, namely the body reflection component 68, which has traveled through the skin and represents skin colors including variations thereof due to the desired vital signals, e.g., heart rate. This reflection component is highly indicative of the signals of interest.

On the contrary, the specular reflection component 64 directly reflected at the top surface 50 of the skin is mainly indicative of the color of the illuminant and does not comprise considerable signals of interest.

Therefore, two fractions of radiance reflected by the object of interest may occur. In combination these fractions form the observed characteristic signals, e.g., the observed color. Illumination conditions may vary over time, e.g., due to object motion. Consequently, also the characteristic signals may vary widely over time.

Figure 3:
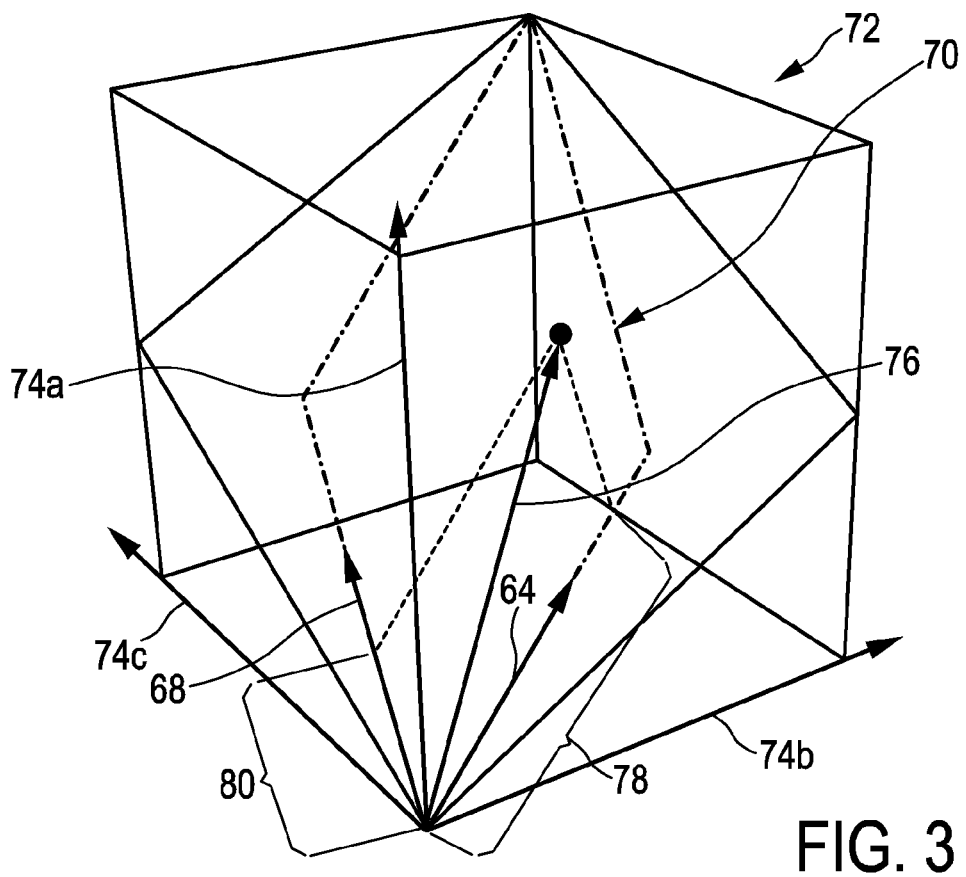
FIG. 3 shows an exemplary schematic illustration of a signal space comprising an index element representing a characteristic signal.

In this connection, FIG. 3 depicts an exemplary signal space 72, e.g. an RGB color space. The signal space 72 comprises additive channels 74a, 74b, 74c indicative of spectral information, e.g., red, green and blue color channels. According to the reflection model outlined above, a detected characteristic signal 76 can be composed of a specular reflection component 64 and a body reflection component 68. The specular reflection component 64 and the body reflection component 68 span a reflection plane 70 in which also the detected characteristic signal 76 can be located. By way of example, the signal space 72 can be considered a "unitary" signal space, wherein components along the additive channels 74a, 74b, 74c can take values between zero and one. Further value ranges departing from the zero and one range can be envisaged and treated accordingly.

For instance, the characteristic signal 76 can be composed according to the following expression:

$$\begin{pmatrix} R_{ch} \\ G_{ch} \\ B_{ch} \end{pmatrix}(i) = m_b(i) \cdot \begin{pmatrix} R_b \\ G_b \\ B_b \end{pmatrix} + m_s(i) \cdot \begin{pmatrix} R_s \\ G_s \\ B_s \end{pmatrix};$$

wherein $(R_{ch}\ G_{ch}\ B_{ch})^T$ can correspond to an RGB value of a detected color pixel along the additive channels 74a, 74b, 74c, wherein $(R_b\ G_b\ B_b)^T$ and $(R_s\ G_s\ B_s)^T$ may denote directions of the body reflection component 68 and a specular reflection component 64, and wherein $m_b(i)$ and $m_s(i)$ can indicate magnitudes 78, 80 of the respective reflection components 64, 68. The term $m_b(i)\cdot(R_b\ G_b\ B_b)^T$ can be considered highly indicative of the desired signal. The term $m_s(i)\cdot(R_s\ G_s\ B_s)^T$ can be considered highly indicative of distortion due to specular reflection.

Besides that, a considerable part of incident radiation 58 can be absorbed by the object's skin tissue. In particular, dark skin color absorbs considerable parts of incident radiation.

Figure 4A:
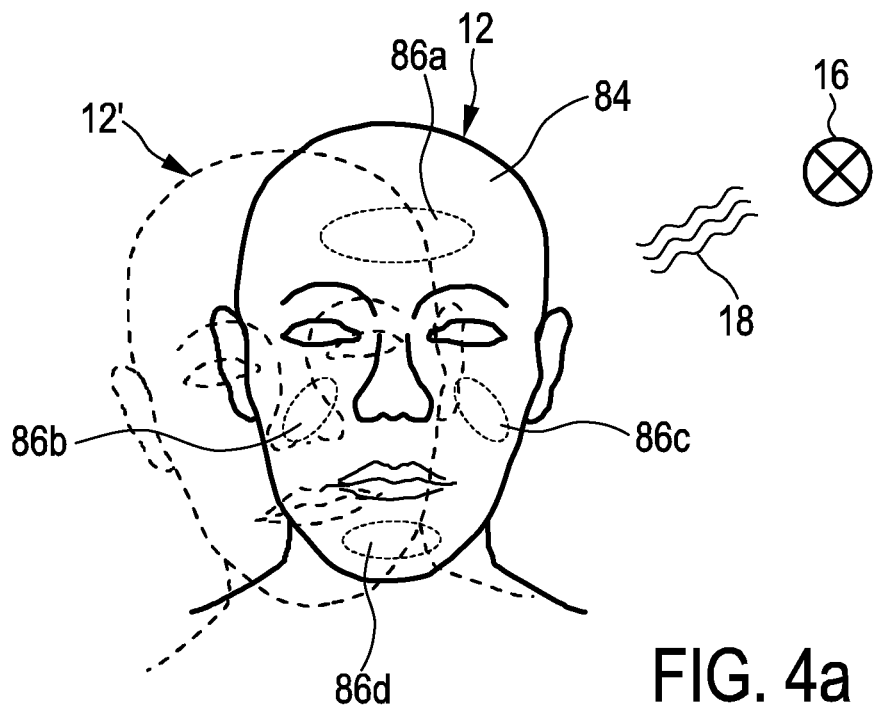
FIGS. 4a and 4b show an object of interest illuminated by a source of electromagnetic radiation, to which an exemplary detection pattern is applied.
Figure 4B:
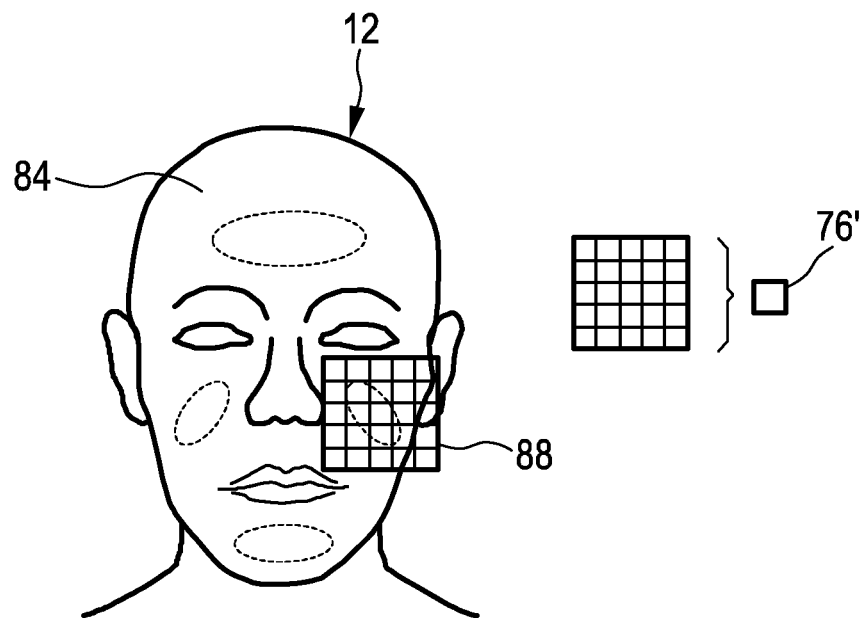

FIG. 4a and FIG. 4b show an exemplary object 12 of interest exposed to incident radiation 18 emitted by a source of radiation 16. Basically, a head portion of the object 12 is illustrated. Skin areas in the head portion which are not covered by hair or otherwise, e.g., due to headgear, glasses, or even makeup, can be considered potentially highly indicative areas 84. It goes without saying that further skin of the object 12 areas not illustrated in FIG. 4a can be drawn for vital signal detection. Dashed lines 86a, 86b, 86c, 86d indicate exemplary face areas which can be susceptible to specular reflections.

It is understood the specular reflection in influenced by a huge number of factors. Therefore, specular reflection is not limited to the areas 86a, 86b, 86c, 86d. Hence, it goes without saying that alternatively the areas 86a, 86b, 86c, 86d can be basically free from specular reflection under certain circumstances. In general, skin areas tending to become greasy or sweaty may reflect main parts of the incident radiation in a specular manner.

A dotted line indicates a shifted object 12'. Object motion can be a major challenge for vital signal detection approaches. Thus, probably a mere detection and "skipping" of areas 86a, 86b, 86c, 86d of specular reflection is considered not to be sufficient for instant signal detection of moving objects 12.

Specular reflection areas 86a, 86b, 86c, 86d basically "mirror" incident radiation or light. In other words, the areas 86a, 86b, 86c, 86d are supposed to have substantially the same additive channel components, e.g., RGB color values, as the emitting source 16.

Thus, the ratio of two of the additive components, e.g., the ratio of red and green, is influenced by the local (detected) specular reflection component 64 in the total reflected radiation, namely the signal of interest 76. Object motion generally changes the average specular reflection component 64 of an area of interest.

FIG. 4b elucidates a common approach to pixel pattern based motion compensation, or, generally, signal normalization. An area of interest of the object 12 of FIG. 4b is masked with an exemplary pixel pattern 88. It is understood that the pixel pattern 88 covers both basically indicative body reflection areas and basically non-indicative specular reflection areas. When agglomerating respective single pixel values of the additive components, a mean pixel value can be derived, namely the mean characteristic signal 76'. The mean characteristic signal 76' can be utilized for further normalization of the detected signals, e.g. the characteristic signals 76, with respect to object motion, at least to a certain extent. However, the detected characteristic signal 76' still comprises a specular reflection portion.

In the following, the signal space 72 and its components can be considered a representation of a certain area of interest of the object 12 which may cover a single pixel or, preferably, an agglomerated pixel area covering a plurality of pixels.

Two essential issues arose when specular reflection is to be taken into account for the desired signal detection. First, the (time based) normalization provided in equation (1) and (2) is no longer applicable and may vary over time since it contains the motion dependent specular reflection component. The second issue is related to the fact that the amplitude of the signal of interest (e.g., HB, i.e. the heart beat) is no longer basically constant as it is proportional only to the fraction of the radiation that is diffusely reflected, namely the body reflection component 68, while the (time based) normalization contains also the specular reflection component 64.

Therefore, remote camera based PPG systems are highly sensitive to motion and/or changing luminance conditions. In the following, an exemplary approach to significantly reduce the effect of specular reflections is outlined. The approach utilizes several aspects of the present invention.

The approach is based on the insight that color difference signals, namely difference components, rather than color signals, namely absolute components, as disclosed in prior art methods, can be drawn for the detection of the vital signals. Hence, the adverse effect of specularly reflected radiation can be eliminated, at least to a certain extent. Consequently, subsequent signal detection profits from a significantly improved signal-noise ratio.

Furthermore, the approach requires less information as luminance information indicative of the strength of the radiation source 16 can be neglected. However, as outlined above, luminance information can be kept for further processing but, at the same time, compressed with a significantly small bit rate without adverse effects on the vital signal detection.

An exemplary numerical description is elucidated in the following. Equation (2) can be rewritten in the following form:

$$\log(1 + HB(i)) = \log\left(\frac{R_n(i)}{G_n(i)}\right) = \log(R_n(i)) - \log(G_n(i)). \tag{3}$$

The logarithmic expression can be approximated by a Taylor expansion:

$$\log(x) = (x-1) - \frac{(x-1)^2}{2} + \frac{(x-1)^3}{3} - \frac{(x-1)^4}{4} + \ldots \tag{4}$$

Hence, assuming that the arguments of the logarithmic terms in Eq. (3) are very close to one, equation (3) finally can be approximated by:

$$HB(i) \approx R_n(i) - G_n(i) \tag{5}$$

Consequently, the desired signal of interest, e.g., the heart rate (or, heart beat), can be extracted from a small signal resulting from the difference, or, so to say the "approximated ratio", of two signals. Both signals $R_n$ and $G_n$ may comprise a large deviation or variance. Therefore, (time based) normalization has to be addressed to with a high level of attention.

With specular reflections the normalization of equation (1) probably contains errors as the skin color differs from the color of the illuminant, the latter representable by the luminance signal 94, or, in other words, the specular reflection component 64. Skin color values can be "distorted", i.e., spatially and/or over time, by the color of the illuminant.

Figure 5A:
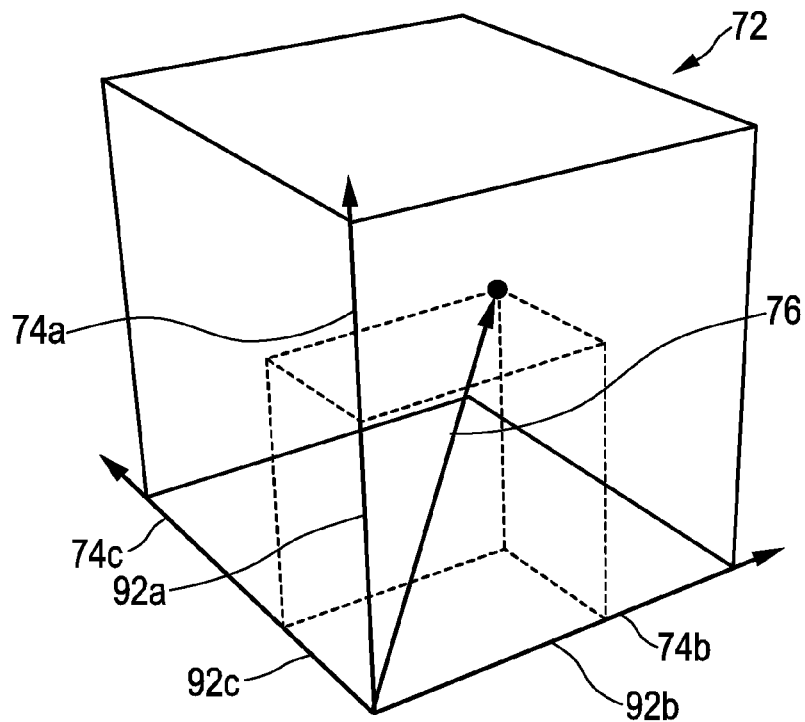
FIGS. 5a and 5b show a further illustration of the signal space according to FIG. 3, the signal space further exhibiting luminance information.

In this connection, FIGS. 5a and 5b and FIGS. 6a and 6b are referred to. FIG. 5a shows a further signal space 72 wherein an exemplary detected characteristic signal 76 is represented by a vector. As the signal space 72 is an additive signal space, the characteristic signal 76 can be composed of (additive) absolute components 92a, 92b, 92c related to respective additive channels 74a, 74b, 74c. For instance, the absolute component 92a can indicate a value along the additive channel 74a which may represent a red channel. The absolute component 92b can indicate a value along the additive channel 74b which may represent a green channel. Eventually, the absolute component 92c can indicate a value along the additive channel 74c which may represent a blue channel. A linear combination of the absolute components 92a, 92b, 92c results in the vector representing the characteristic signal 76.

Figure 5B:
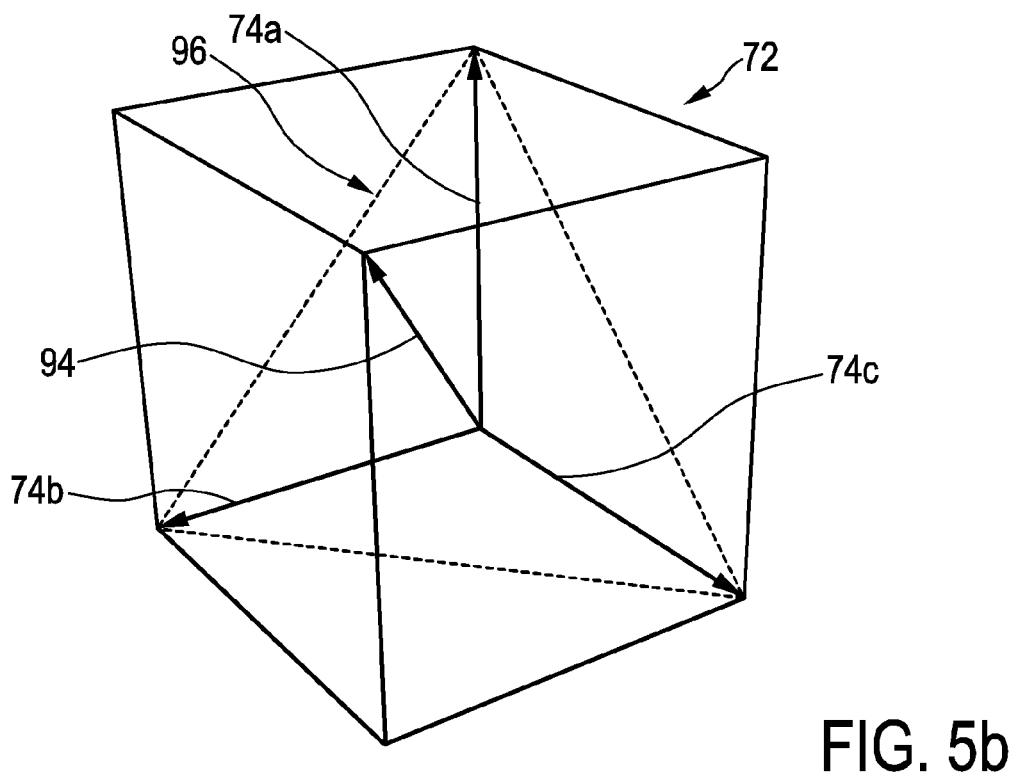

In FIG. 5b a signal space 72 according to FIG. 5a is basically rotated by some 180° around the axis representing the additive channel 74a for illustrative purposes. Assuming that the specular reflection component 64 of FIG. 2 is a mirror-like reflection of incident radiation or light, a luminance signal 94 can be introduced basically traversing the signal space 72 as a diagonal vector. This applies in particular when the radiation source 16 basically emits plain white light. Preferably the "color" of the radiation source 16 equals the white point of the signal space. In case the whole area of the object 12 which is monitored undergoes permanent specular reflection, the characteristic signal 76 contains no further component besides the luminance signal 94. Furthermore, given this assumption, the length of the luminance signal 94 equals the overall diagonal dimension of the signal space 72. However, in this case no diffuse body reflection component 68 can be extracted.

The luminance signal is basically perpendicular to a chrominance plane 96. The chrominance plane 96 is a diagonal plane in the signal space 72. For instance, the chrominance plane 96 can be described by the expression R+G+B=1, wherein $0 \leq R \leq 1$, $0 \leq G \leq 1$ and $0 \leq B \leq 1$. When aiming at an elimination of luminance information from the characteristic signal 76, graphically a projection to the chrominance plane 96 can be sought-for.

Figure 6A:
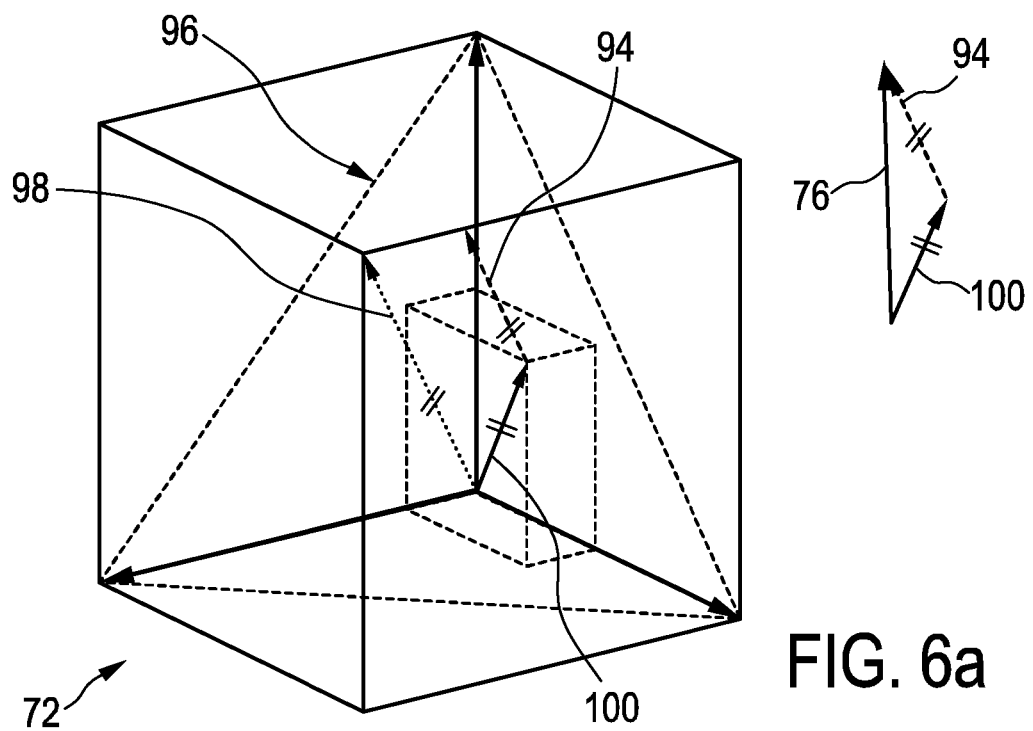
FIGS. 6a and 6b show a further illustration of the signal space according to FIG. 3, FIGS. 7a and 7b show an exemplary schematic illustration of a simplified signal space by way of explanation.
Figure 6B:
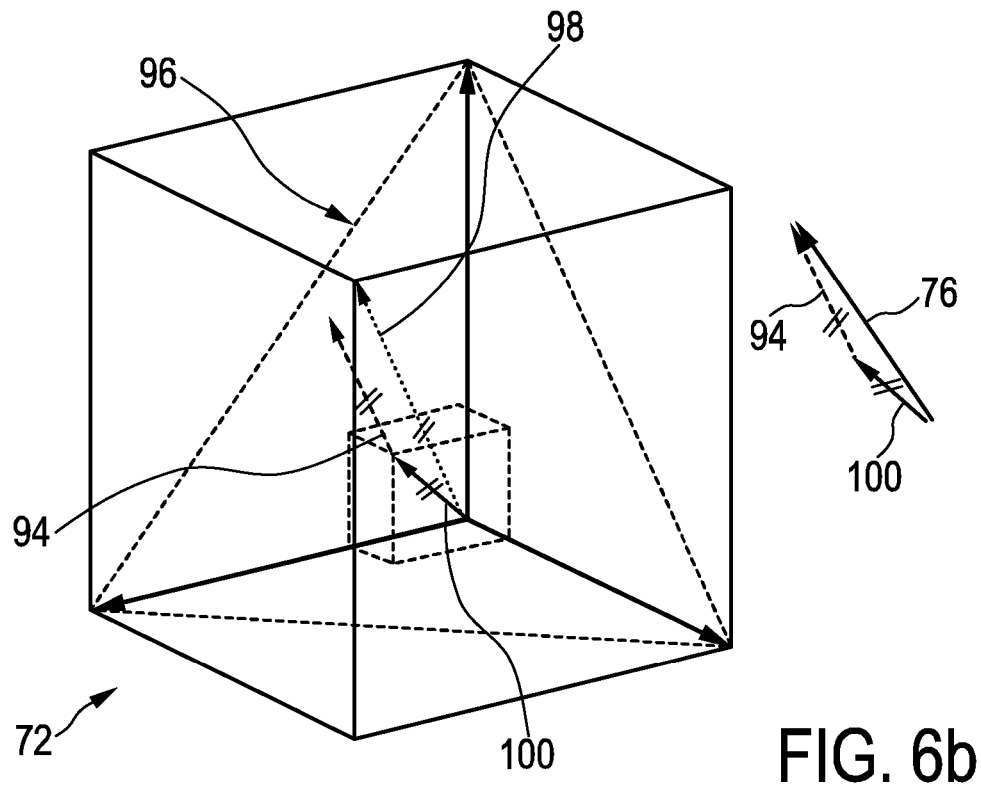

Based of FIG. 5b, FIG. 6a and FIG. 6b show further signal spaces 72 comprising luminance signals 94 indicative of specular reflection components and physiological information signals 100 indicative of (diffuse) body reflection components. For illustrative purposes, also linear combinations, namely the composed characteristic signals 76, of the vector components 94, 100 are presented next to the respective signals spaces 72. In this context, it is reminded that FIGS. 6a and 6b represent a three-dimensional (3D) representation. Consequently, also the added linear combinations represent 3D vectors rather than two-dimensional (2D) vectors.

In FIGS. 6a and 6b a luminance index element 98 is shown. The luminance index element 98 can be considered a diagonal vector traversing the signal space 72. In case the luminance signal 94 is only partially influencing a detected area of interest, e.g., the pixel pattern 88, the luminance signal 94 is "shorter" than the luminance index element 98. Both vectors, the luminance signal 94 and the index element 98 are parallel and point in the same direction. The luminance index element 98 is indicative of the radiation source. The luminance signal 94 can be considered an expression of how much the detected area of interest, e.g., the pixel pattern 88, is influenced by specular reflection.

It would be advantageous to decompose the characteristic signals 76 so as to arrive at the desired physiological information signals 100. Substantially, the orientation and length of the desired physiological information signals 100 is unknown. While the orientation of the luminance signals 94 is basically known, the length of the luminance signals 94 is also unknown.

Therefore, the current approach relies on color difference signals instead of color signals. Since the specular reflection component is substantially identical in all color signals, e.g., roughly white illuminant, it can be considered absent in the difference of two color signals. It is reminded that the color signals may be represented by the respective values of the absolute components 92a, 92b, 92c, e.g., $(R_{ch}\ G_{ch}\ B_{ch})^T$, of the characteristic signal 76.

It is understood that the amplitude of a single color difference signal can still be proportional to the strength of the illuminant. Therefore, at least two color difference signals, e.g., $\Delta_1$ and $\Delta_2$, are required for eliminating variation in the strength of the illumination, e.g., caused by object motion. Consequently, they have to be derived from at least three color signals. Therefore, the additive RGB space can be considered a proper choice since the characteristic signal 76 is composed of three absolute color components 92a, 92b, 92c. Preferred transformations and coefficients are outlined above.

Figure 7A:
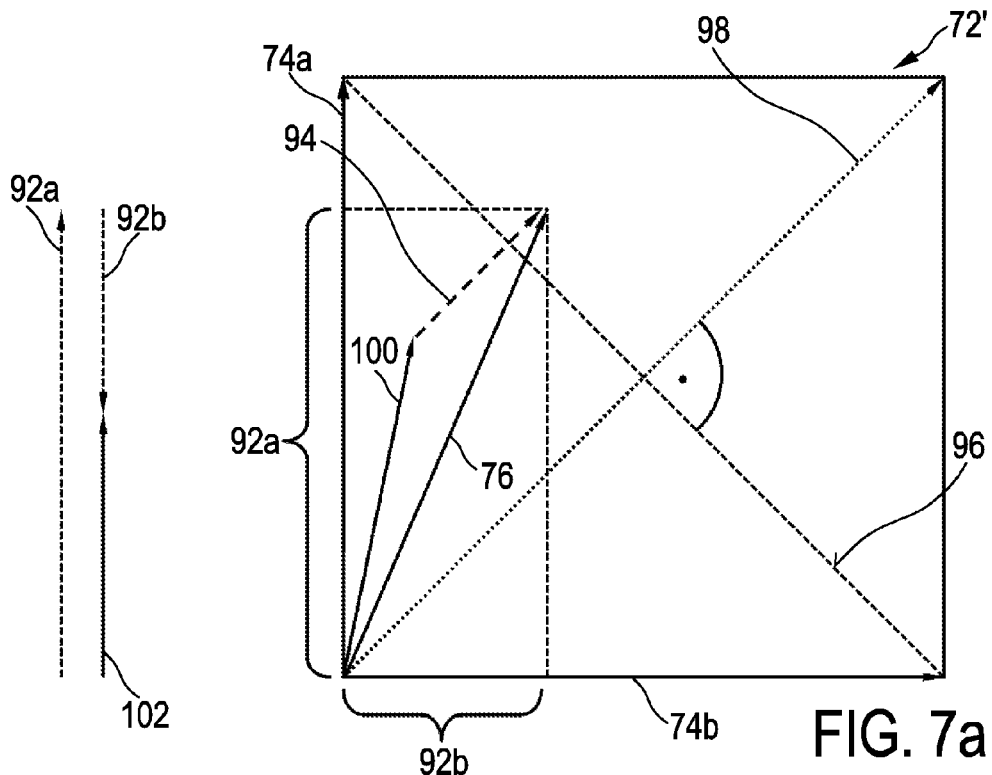
Figure 7B:
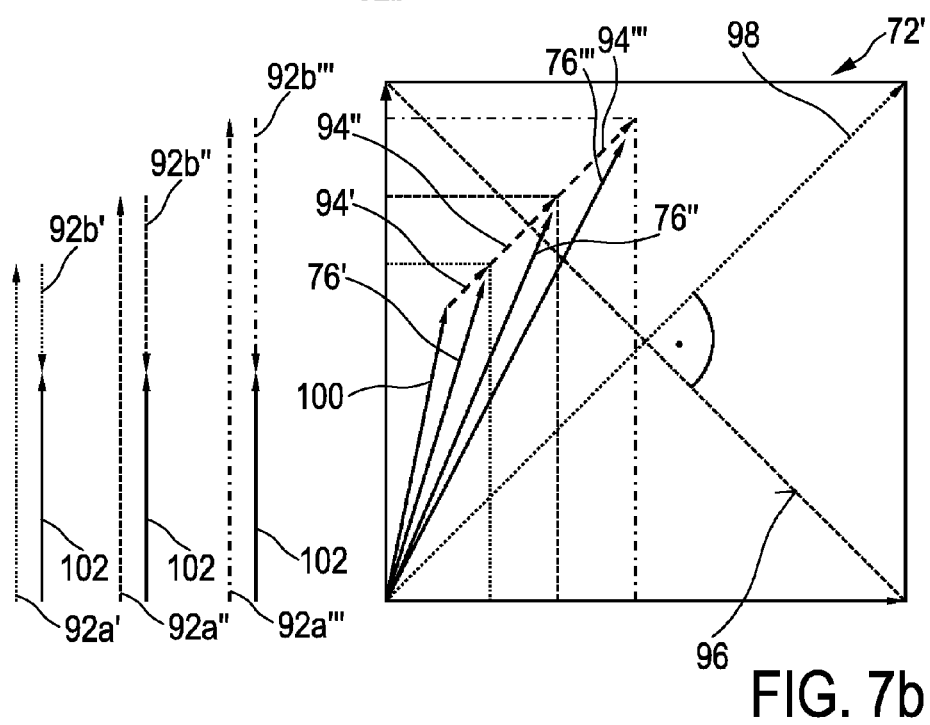

FIGS. 7a and 7b are referred to. Merely for illustration purposes both FIG. 7a and FIG. 7b show two-dimensional (2D) signal spaces 72'. In others words, the signal spaces 72' can be considered "slices" of the signal space 72. Therefore, the chrominance plane 96 is represented as a diagonal line being perpendicular to the luminance index element 98. Reference numerals 74a, 74b indicate two of the at least three additive channels, e.g., red and green out of the RGB signal space. In FIG. 7a a characteristic signal 76 is represented comprising two components, namely the luminance signal 94 and the physiological information signal 100. The luminance signal 94 is parallel to the luminance index element 98. Reference numerals 92a, 92b indicate absolute components of the characteristic signal 76.

Next to the signal space 72' of FIG. 7a a simple arithmetic transformation is illustrated by means of the magnitudes (lengths) of the absolute components 92a, 92b. Reference numeral 102 indicates a difference component derived from both absolute components 92a, 92b. Put differently, the difference component $\Delta$, can be obtained by applying the exemplary expression $\Delta_1 = 1 \cdot R_{ch} + (-1) \cdot G_{ch}$.

FIG. 7b is based on FIG. 7a. For the characteristic index elements 76', 76", 76''' the physiological information signal 100 is kept stable while the luminance signals 94', 94", 94''' are varied. Hence, the characteristic index elements 76', 76", 76''' become distorted. However, the respective absolute components 92a', 92b'; 92a", 92b"; 92a''', 92b''' vary accordingly. Thus, when applying the expression provided above, the difference component 102 remains unchanged. Consequently, varying illumination conditions have no adverse effects on subsequent signal extraction measures.

As mentioned above, for some applications the normalization of the color difference signals $\Delta_1$ and $\Delta_2$, analog to equation (1), potentially cannot be carried out. This applies in particular when selected (temporal frequency) portions of the difference components, eventually also their temporal mean values, are either enhanced or suppressed. Basically, the mean values can be leveled in this manner. Furthermore, it can be assumed that the mean signals no longer exhibit the slight (at least partially periodic) changes of the original signals indicating the desired vital information. In other words, the signal means potentially can become zero. Hence, division by the temporal mean values can pose a division by zero issue. Therefore, an estimation of the ratio of the at least two difference components can result in computing problems. For this reason, the derivation provided in equations (3), (4) and (5) can be applied. Consequently, the mere ratio of the difference components can be replaced by a difference, e.g., $HB(i) \approx \Delta_1(i) - \Delta_2(i)$. However, for some applications the normalization of $\Delta_1$ and $\Delta_2$ in accordance with equations (1) and (2) is a suitable alternative. This applies in particular in case the whole genuine frequency band of the original signals is utilized for normalization.

A further refinement may comprise a minimization of the variance of a weighted sum of the two difference components. Hence, (time-based) normalization can be improved. This approach can compromise applying a weighting function to the at least two difference components:

$$HB(i) \approx \Delta_1(i) - w(i)\Delta_2(i), \quad (6)$$

wherein the weight can be selected in order to minimize the variance of the vital signal of interest, e.g., the heart rate. Various approaches can be envisaged. A fairly simple method determines w(i) in such a way that the standard deviation of the two terms in equation (6) are basically equal:

$$w(i) = \frac{std(\Delta_1)}{std(\Delta_2)}. \quad (7)$$

In this way, overall disturbances can be removed from the desired signal to a certain extent. For instance, the standard deviation can be calculated in a temporal window around i. By way of example, the window can be chosen in the order of about one second. Hence, the number of frames to be covered by the moving window can be derived therefrom.

Furthermore, the resulting signal of interest, e.g. the heart rate, can be further normalized by applying its standard deviation. Advantageously, the standard deviation can be calculated utilizing the same window size interval as chosen for the weighting function.

Figure 8:
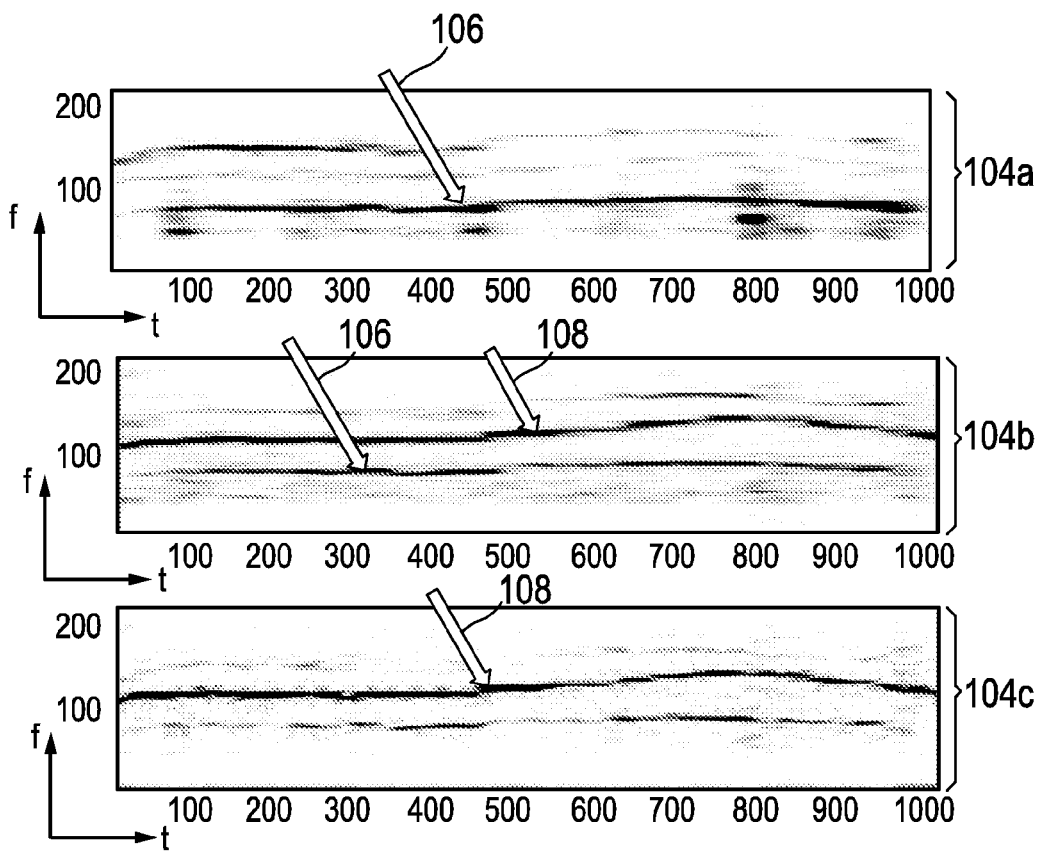
FIG. 8 depicts three diagrams, each showing a spectrogram of physiological information obtained from an object of interest in a first exemplary case of application.
Figure 9:
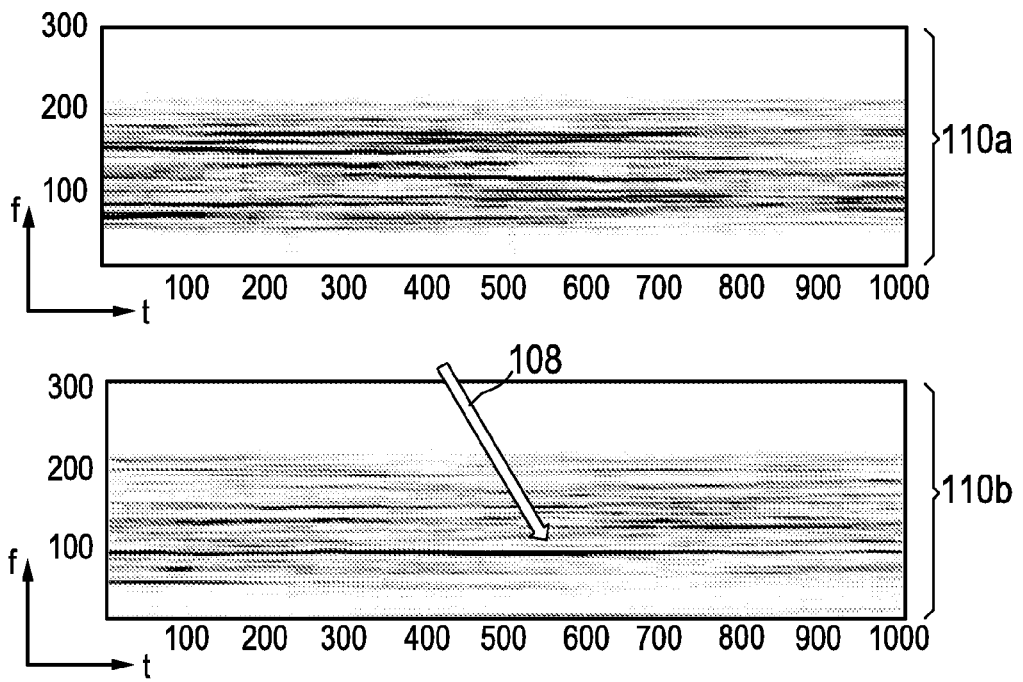
FIG. 9 depicts two diagrams, each showing a spectrogram of physiological information obtained from an object of interest in a second exemplary case of application.

Reference is made to FIG. 8 and FIG. 9 showing exemplary spectrograms illustrating results of remote photoplethysmographic analyses utilizing several approaches. In the diagrams, f denotes frequency while t denotes time. The frequency axis can represent Hz (Hertz) values while the time axis may stand for the number of processed image frames.

The spectrograms 104a, 104b, 104c of FIG. 8 exemplify the same situation, namely results obtained from a person performing some workout on a fitness device. Under these circumstances, objection motion renders the detection challenging. Furthermore, as the skin typically becomes sweaty during a workout, strenuous activities basically may imply further adverse effects on the detected characteristic index elements the desired signal is to be derived from.

The spectrogram 104a represents a basic PPG approach relying on (absolute) color components, namely red and green values. The spectrogram 104a merely exhibits one dominant frequency 106. However, this dominant frequency 106 is indicative of undesired object motion, e.g., the fitness exercise motion, rather than the desired signal(s) of interest.

Based on the same input data, the spectrogram 104b represents the difference component approach outlined above. Consequently, two dominant frequencies 106, 108 can be detected. Besides the stepping frequency 106 also the desired vital signal of interest 108, namely the heart rate, can be detected. The spectrogram 104c represents further refinements leading to an even further enhanced dominant frequency 108 while the motion-related dominant frequency 106 is suppressed. Consequently, the difference component approach enhances the signal-to-noise ratio, even under poor conditions.

FIG. 9 provides two spectrograms 110a, 110b exemplifying remote photoplethysmographic analyses directed to an object having very dark skin. The spectrogram 110a representing a basic photoplethysmographic approach is dominated by noise. The spectrogram 110b relies on photoplethysmography utilizing difference components rather than absolute components. It can be clearly seen that a dominant frequency 108 indicative of the desired signals has been enhanced so as to allow further signal processing.

Figure 10:
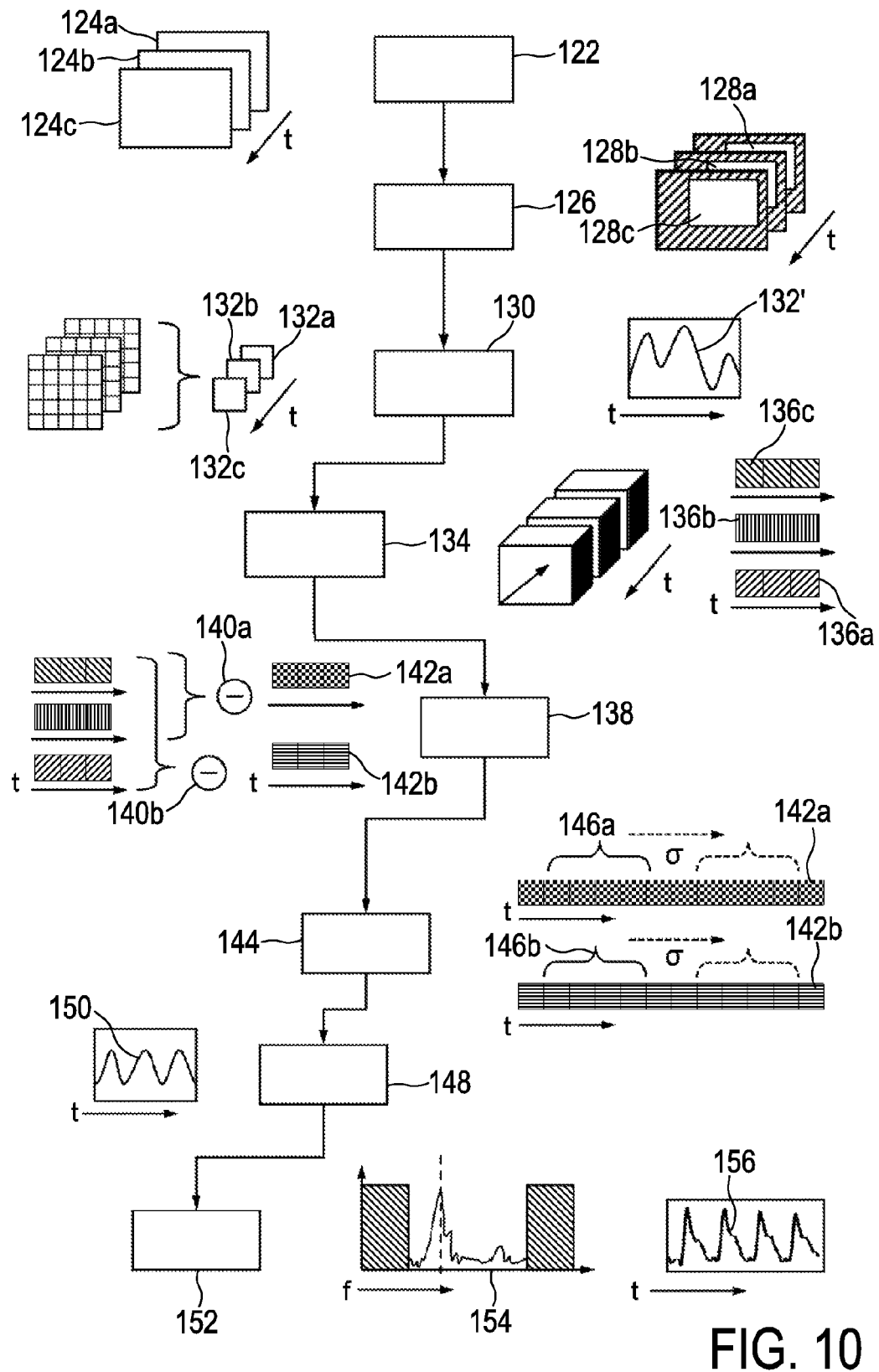
FIG. 10 shows an illustrative block diagram representing several steps of an embodiment of a method according to the invention.

Having demonstrated several alternative exemplary approaches covered by the invention, FIG. 10 is referred to, schematically illustrating a method for extracting information from characteristic signals.

Initially, in a step 122 an input data stream or sequence comprising several frames 124a, 124b, 124c is received. A time axis is indicated by an arrow t. The data stream can be delivered from the sensor means 24 or a data buffer or storage means. The data stream can be embodied, by way of example, by a sequence of image frames varying over time. The image frames can comprise RGB based pixel data. The data steam comprises a representation of an object of interest.

In a subsequent step 126 portions of interest 128a, 128b, 128c can be selected in the data stream. The portions of interest 128a, 128b, 128c may comprise skin portions of an object on interest, e.g., a face portion of a human being to be observed. Non-indicative portions, e.g., clothes, hair, or further non-indicative surroundings, can be removed from the data stream. According to an exemplary embodiment, the portions of interest 128a, 128b, 128c can be selected and tracked by means of face detection. Furthermore, step 126 can comprise motion compensation measures directed to object motion and/or sensor means motion. Consequently, the problem of extracting the desired information can be facilitated In a further step 130 a detected pattern, e.g., the portions of interest 128a, 128b, 128c of data stream image frames, are normalized. Suitable approaches have been outlined above. By way of example, a pixel array having a certain dimension can be summarized in a single entity representative of mean values of image characteristics of the whole pixel array. The resulting normalized signal is indicated by 132a, 132b, 132c. When applying the RGB color space, the normalized entity can comprise mean red, green and blue values. An exemplary representation of the normalized signal over time is indicated for illustrative purposes by reference numeral 132'. The normalized signal 132' comprises indicative and non-indicative portions. The non-indicative portion can be attributed to specular reflection of incident electromagnetic radiation, at least partially. The indicative portion can be attributed to diffuse reflection of incident electromagnetic radiation, at least partially.

In an even further step 134, the normalized signal 132' is split up into additive components 136a, 136b, 136c from which it is composed. By way of example, the additive components 136a, 136b, 136c can represent red, green and blue values. It goes without saying, that the additive composition can be inherent to the normalized signal 132' or the input data stream. Therefore, alternatively, step 134 can be considered an illustrative step facilitating understanding. Viewed in terms of vector representation, vectors representing the normalized signal 132' in the signal space, e.g., RGB, are split up into their components.

In a further subsequent step 138, an arithmetic transformation is applied to the additive components 136a, 136b, 136c. The arithmetic transformation results in difference components 142a, 142b. The difference components 142a, 142b comprise chrominance information rather than luminance information. The arithmetic transformation utilizes coefficients substantially summing to zero. By way of example, the difference component 142a is derived through a transformation of the additive channels 136b, 136c. The transformation can be embodied by an addition comprising positive and negative coefficients summing to zero. The transformation results in "difference" values. Therefore, the transformation is indicated by a subtractive operator 140a. Similarly, difference component 142b can be derived through a transformation of the additive channels 136a, 136b, 136c. The transformation is indicated by a subtractive operator 140b. Possible formulas and coefficients have been outlined above.

Eventually, the non-indicative (specular) reflection portion is suppressed in the difference components 142a, 142b as luminance information is "deducted", at least to some extent. In this way, the specular reflection portion can be minimized or even removed from the initial signal.

In a further step 144 a deviation value or variance value, e.g., the standard deviation a or possible derivates thereof, is determined for each of the difference components 142a, 142b. To this end, moving windows 146a, 146b are applied to the time signal of the difference components 142a, 142b.

In a subsequent step 148 the calculated deviation values are utilized for carrying out a weighting function. The weighting can be applied to the difference components 142a, 142b. Additionally, a signal 150 can be composed taking into account the (weighted) difference components 142a, 142b. The weighting can be directed to minimize a variance of the composed signal 150. The composed signal 150 is highly indicative of the desired signals, e.g., heart rate or heat rate variability.

In a further step 152, further analyzing measures are applied to the composed signal 150. Finally, the desired signals can be extracted therefrom. For instance, a temporal pulsation in the composed signal 150 is sought-for. The analyzing measures can comprise spectral analysis or frequency analysis. Reference numeral 154 depicts an exemplary spectral representation of the composed signal 150. The spectral representation exposes a dominant frequency. A frequency axis is indicated by an arrow f. Furthermore, a time-based representation of a signal of interest 156 might be of interest.

By way of example, the present invention can be applied in the field of health care, e.g. unobtrusive remote patient monitoring, general surveillances, security monitoring and so-called lifestyle applications, such as fitness equipment, or the like. Applications may include monitoring of oxygen saturation (pulse oxymetry), heart rate, respiration rate, blood pressure, cardiac output, changes of blood perfusion, assessment of autonomic functions and detection of peripheral vascular diseases.

Needles to say, in an embodiment of a method in accordance with the invention several of the steps provided can be carried out in changed order, or even concurrently. Further, some of the steps could be skipped as well without departing from the scope of the invention. This applies in particular to several alternative signal processing steps.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the words "comprising" and "including" do not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Device for extracting information from detected characteristic signals, comprising:
   an interface for receiving a data stream derivable from electromagnetic radiation reflected by an object, wherein the data stream comprises a characteristic signal including (i) physiological information and (ii) a disturbing signal portion, the physiological information being representative of at least one at least partially periodic vital signal, the disturbing signal portion being representative of at least one selected from the group consisting of an object motion portion and a non-indicative reflection portion, wherein the characteristic signal is associated with an additive signal space, wherein the signal space comprises additive channels for representing the characteristic signal;
   a converter means for transferring the characteristic signal into a transferred signal by converting (i) at least three absolute components of the characteristic signal related to respective additive channels to (ii) at least two difference components of the characteristic signal, wherein each of the at least two difference components is derived through a respective arithmetic transformation that comprises an at least partial subtraction of at least one of the at least three absolute components from the remaining absolute components, wherein the arithmetic transformation for each of the at least two difference components further comprises coefficients that at least substantially sum to zero, and further wherein the at least two difference components enable the disturbing signal portion to be at least partially suppressed in the transferred signal; and an extractor means for extracting the at least partially periodic vital signal from the at least two difference components in the transferred signal.

2. Device as claimed in claim 1, wherein the signal space is an additive color signal space, wherein the at least three absolute components represent three distinct color components indicated by the additive channels, wherein the additive channels are related to defined spectral portions.

3. Device of claim 2, wherein the signal space is further indicative of luminance information and chrominance information, the chrominance information being representable by the at least two difference components.

4. Device of claim 3, wherein the luminance information is substantially aligned with a luminance index element in the signal space, the luminance index element being substantially indicative of a selected source of electromagnetic radiation.

5. Device of claim 4, wherein the at least two difference components are substantially orthogonal to the luminance index element.

6. Device of claim 5, further wherein the at least two difference components are substantially orthogonal to each other.

7. Device as claimed in claim 1, wherein the at least one at least partially periodic vital signal is selected from the group consisting of heart rate, heart beat, respiration rate, heart rate variability, Traube-Hering-Mayer waves, and oxygen saturation.

8. Device of claim 1, further comprising a weighting means for weighting the at least two difference components so as to derive a weighted transferred signal from the transferred signal under consideration of at least two weighted difference components.

9. Device of claim 8, wherein the weighting comprises a determination of a deviation value of each of the at least two difference components, and wherein the deviation value of each of the at least two difference components is determined under consideration of temporal variations thereof over a moving window applied to a sequence of each of the at least two difference components.

10. Device of claim 9, wherein the deviation value is a standard deviation.

11. Device of claim 8, wherein the weighting is directed to minimize a spread of the weighted transferred signal.

12. Device of claim 1, wherein at least one of the converter means and the extractor means is further adapted to normalize the transferred signal under consideration of a deviation value thereof, preferably a standard deviation, over a moving window applied to a sequence of the transferred signal.

13. Device of claim 12, wherein the deviation value is a standard deviation.

14. Device as claimed in claim 1, further comprising an analyzing means, the analyzing means being comprised in the extractor means or coupled thereto, wherein the analyzing means is adapted for a frequency analysis of the at least one at least partially periodic vital signal.

15. Device as claimed in claim 14, further comprising a processing unit that comprises the converter means, the extractor means and the analyzing means.

16. Device as claimed in claim 15, wherein at least one of the converter means, the extractor means and the analyzing means is further adapted for delivering a compressed output signal, wherein the compressed output signal comprises the luminance information represented by a luminance signal and the chrominance information represented by the at least two difference components, wherein selective compression rates are applied to the luminance information and the chrominance information, and wherein the chrominance information is compressed to a lower compression factor than the luminance information.

17. Device of claim 14, wherein the analyzing means is further adapted for filtering the processed transferred signal and for enhancing a signal component at a bandwidth between 0.2 Hz and 10 Hz.

18. Device of claim 17, wherein the bandwidth further comprises between 0.5 Hz and 3.5 Hz.

19. Method for extracting information from detected characteristic signals, comprising the steps:
receiving a data stream derivable from electromagnetic radiation reflected by an object, wherein the data stream comprises a characteristic signal including (i) physiological information and (ii) a disturbing signal portion, the physiological information being representative of at least one at least partially periodic vital signal, the disturbing signal portion being representative of at least one selected from the group consisting of an object motion portion and a non-indicative reflection portion, wherein the characteristic signal is associated with an additive signal space, wherein the signal space comprises additive channels for representing the characteristic signal;
transferring the characteristic signal into a transferred signal by converting (i) at least three absolute components of the characteristic signal related to respective additive channels to (ii) at least two difference components of the characteristic signal, wherein each of the at least two difference components is derived through a respective arithmetic transformation that comprises an at least partial subtraction of at least one of the at least three absolute components from the remaining absolute components, wherein the arithmetic transformation for each of the at least two difference components further comprises coefficients that at least substantially sum to zero, and further wherein the at least two difference components enable the disturbing signal portion to be at least partially suppressed in the transferred signal; and
extracting the at least partially periodic vital signal from the at least two difference components in the transferred signal.

20. A non-transitory computer-readable medium embodied with a computer program comprising program code for causing a computer to carry out the steps of the method as claimed in claim 19 when said computer program is carried out on the computer.

* * * * *